United States Patent [19]

Pritchard et al.

[11] 3,990,117
[45] Nov. 9, 1976

[54] ELBOW JOINT PROSTHESIS

[76] Inventors: Rowland W. Pritchard, 205 French St., Bangor, Maine 04401; Peter S. Walker, Apt. 10D, 1161 York Ave., New York, N.Y. 10021

[22] Filed: Jan. 22, 1975

[21] Appl. No.: 543,133

[52] U.S. Cl. .................................. 3/1.91; 128/92 C
[51] Int. Cl.² ........................................... A61F 1/24
[58] Field of Search ..................... 3/1, 1.9–1.911; 128/92 C, 92 CA, 92 R

[56] References Cited
UNITED STATES PATENTS

| | | |
|---|---|---|
| 3,728,742 | 4/1973 | Averill et al. .......................... 3/1.91 |
| 3,765,033 | 10/1973 | Goldberg et al. ..................... 3/1.911 |
| 3,772,709 | 11/1973 | Swanson ................................ 3/1.91 |
| 3,813,700 | 6/1974 | Tavernetti et al. ............. 128/92 C X |
| 3,837,009 | 9/1974 | Walker ............................... 3/1.911 |

OTHER PUBLICATIONS

"Arthroplasty of the Knee" by L. Shiers, *The Journal of Bone & Joint Surgery*, vol. 36B, No. 4, Nov. 1954, pp. 553–560.

*Primary Examiner*—Ronald L. Frinks
*Attorney, Agent, or Firm*—Woodard, Weikart, Emhardt & Naughton

[57] ABSTRACT

An implantable prosthetic joint, particularly suitable for use as an elbow joint, comprising a first component and a second component, each of which includes a stem implantable in bone. The first component has a head portion whose end is essentially spheroid, the head portion being slotted and having a transverse bore therethrough. The second component has a head-engaging portion including a protuberant disc-shaped portion received in the slot of the head portion of the first component. A transverse bore in the protuberant portion is aligned with the bore in the head portion of the first component, and a pin assembly is positioned within the bores for hingedly attaching the first and second components. The head-engaging portion of the second component includes overlying shoulders which receive the ball-shaped head portion of the first component on either side of the slot. The bore through the protuberant portion of the second component is of greater diameter than the diameter of the pin assembly at that point, permitting wobble of the second component relative to the first component. When this wobble, or transverse rocking motion, of the joint occurs, the spheroid end of the head portion of the first component bears against the receiving shoulders of the second component rather than exerting forces on the pin assembly.

10 Claims, 8 Drawing Figures

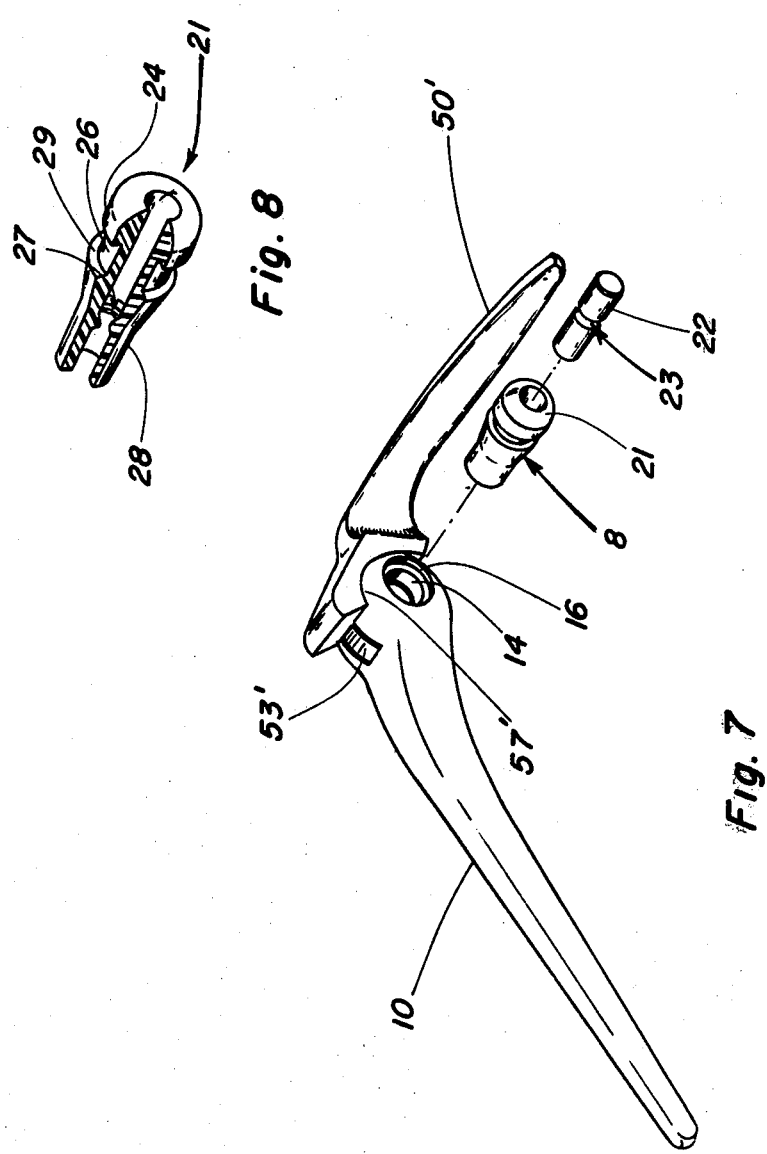

ELBOW JOINT PROSTHESIS

BACKGROUND OF THE INVENTION

1. Field of the Invention

The invention is in the field of bone prostheses.

2. Description of the Prior Art

In the past, many types of joint prostheses have been proposed. Among these are "ball-and-socket" joints, many of which include means for limiting the motion of the joint components relative to one another to essentially a single plane. Such "ball-and-socket" joints may be found in U.S. Pat. Nos. 3,760,427 to Schultz; 3,694,821 to Moritz; 3,651,521 to Devas; 3,638,243 to Campbell et al.; and 3,506,982 to Steffee. The Campbell and Devas joint prostheses are particularly described for use as elbow joint prostheses. Neither of these prostheses utilize a hinge pin to provide positive hinged motion and component retention. The Campbell prosthesis includes provision for axial rotational motion of the joint components relative to one another through freedom of the stem of the ball member to rotate partially in the slot of the socket member.

Various hinged elbow prostheses have also been proposed, relying upon the hinge pin for load bearing and not permitting any appreciable degree of "wobble" or rocking movement of one joint component relative to the other. Such joint prostheses are disclosed in U.S. Pat. Nos. 3,816,854 to Schlein; 3,772,709 to Swanson; 3,708,805 to Scales et al.; and 3,656,186 to Dee. Many of these prostheses are large and require resection of large parts of the natural joint. In such cases, any subsequently required prostheses of the same joint may be difficult or impossible.

SUMMARY OF THE INVENTION

One embodiment of the present invention is an implantable prosthetic joint comprising a first component including, a first stem portion for affixing the first component to bone, a head portion on one end of the first stem portion, the end of the head portion furthest from the first stem being generally curved, said head portion including a slot and also including a bore through said head portion transverse to and intersecting said slot, a second component including, a second stem portion for affixing the second component to bone, a head-engaging portion including a protuberant portion having a thickness less than that of said slot, said protuberant portion being received in the slot and having a bore therethrough aligned with the transverse bore of the head portion of the first component, the head-engaging portion further including a shoulder portion on each side of said protuberant portion receiving the generally curved head portion of the first component on either side of said slot, and pin means extending through the bores of the protuberant portion and the head portion for attaching the first component to the second component, such that hinge-like motion between the two components is permitted, and for permitting a limited degree of motion of the components relative to one another in directions transverse to the plane of said hinge-like motion.

It is an object of the present invention to provide a hinged joint prosthesis which has a limited degree of "whobble" between the joint components and which includes load bearing at the joint principally between the joint components rather than upon the hinge pin assembly.

It is a further object of the present invention to provide such a joint prosthesis which includes a snap-in hinge pin assembly.

It is a further object of the present invention to provide such a joint prosthesis which is particularly adapted for use as an elbow joint prosthesis and which is relatively small and positionable with a minimum removal of bone structure at the joint, particularly in regard to the olecranon process.

Further objects and advantages of the present invention shall be apparent from the following detailed description and accompanying figures.

BRIEF DESCRIPTION OF THE DRAWINGS

FIG. 7 is an exploded perspective view of a joint prosthesis utilizing components similar to those of FIGS. 1 through 6, showing the pivot pin and bearing pin comprising the pin assembly.

FIG. 8 is an enlarged cutaway view of the bearing pin of FIG. 7.

DESCRIPTION OF THE PREFERRED EMBODIMENT

Figure 1:
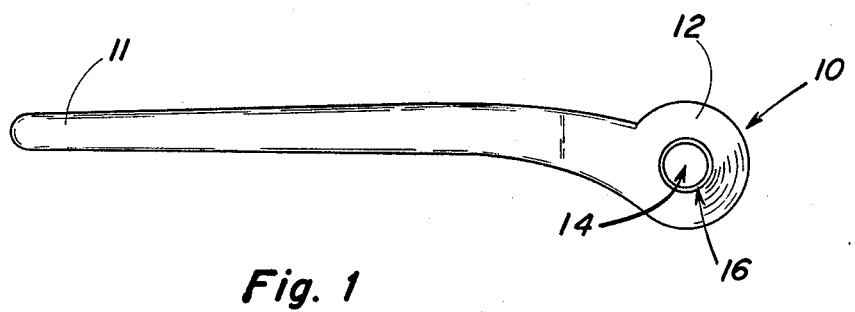
FIG. 1 is a side view of the humeral component of an elbow joint prosthesis according to the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 2:
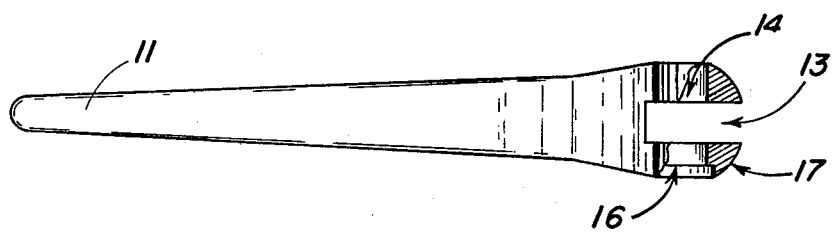
FIG. 2 is a top view of the humeral component of FIG. 1 with part of the head portion removed.

Referring in particular 4½ FIGS. through 3, there is shown a humeral component ¾ for an elbow joint prosthesis according to the present invention. Humeral component 10 includes a stem portion 11 for insertion into the humerus and a head portion 12. As can be seen in the figures, head portion 12 is essentially spheroid at its end furthest from the stem 11. There is a slot 13 in head portion 12 to receive a protuberant portion of the ulnar component, as shall be explained infra. Head portion 12 further includes a bore 14 transverse to slot 13 and intersecting slot 13. Transverse bore 14 receives a bearing pin assembly for the hinged joint as shall be described more particularly hereinafter. At one end of transverse bore 14, there is an enlarged portion 16, as shown in FIGS. 1 and 2, to receive the head portion of the bearing pin assembly. Humeral component 10 is preferably constructed of an ultra high molecular weight polyethylene material, and the same humeral component is used in both the right and left arm in joint prostheses. The humeral component shown in FIGS. 1 through 3 for use in an elbow joint prosthesis is preferably about 4 1/2 to 5 inches long and about 3/4 of an inch in diameter at the head portion.

Figure 3:
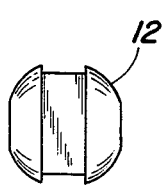
FIG. 3 is an end view of the humeral component of FIG. 1.
Figure 4:
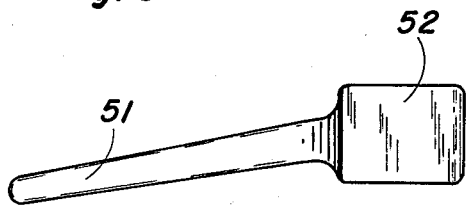
FIG. 4 is a bottom view of an ulnar component for use with the humeral component of FIG. 1.
Figure 6:
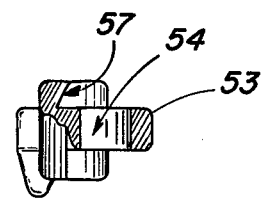
FIG. 6 is an end view of the ulnar component of FIG. 4, with part of the head-engaging portion removed.
Figure 5:
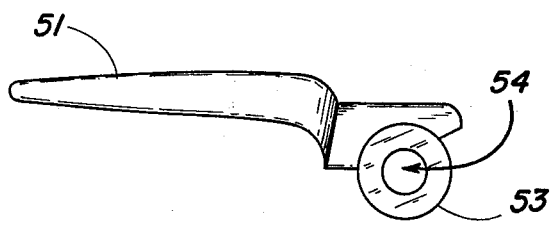
FIG. 5 is a side view of the ulnar component of FIG. 4.

Referring now to FIGS. 4 through 6, there is shown an ulnar component 50 for use with the humeral component 10 of FIGS. 1 through 3 in an elbow joint prosthesis. Ulnar component 50 includes a stem portion 51 for insertion into the ulna and a head-engaging portion 52. Head engaging portion 52 includes a protuberant disc portion 53 which is received within slot 13 of the head 12 of humeral component 10. A transverse bore 54 through protuberant portion 53 is aligned with bore 14 of head 12 when the joint is assembled with protuberant portion 53 within slot 13.

As shown in FIG. 6, concave shoulders such as 57 extend beyond either side of protuberant portion 53. When the joint prosthesis is assembled, shoulders 57 are engaged by the end 17 of head 12 of the humeral component on either side of the slot 13. This provides end load-bearing of the generally spherical surfaces of head 12 against the shoulders 57. Bore 54 through protuberant portion 53 of ulnar component 50 is of greater diameter than the bearing pin assembly passing through bores 14 and 54 which permits wobble, or rocking, of head-engaging portion 52 against head 12 with the load-bearing and engagement between spheroid end portion 17 and shoulders 57. As can be seen, this provides, to a limited degree, a ball and socket type of joint while retaining the strength and positive holding of a hinge joint prosthesis.

The ulnar component 50 shown in FIGS. 4 through 6 is an ulnar component for a right arm. As shown in FIG. 4, stem portion 51 of ulnar component 50 is at an angle from the center line of head engaging portion 54 of preferably about 11°. This angling would be in the opposite direction, upward rather than downward as viewed in FIG. 4, for a left arm ulnar component. Ulnar component 50 is stainless steel or other similar surgically approved metal and is about 3 inches long and ⅝ of an inch wide at the head-receiving portion.

Referring now to FIG. 7, there is shown an exploded view of a joint prosthesis utilizing components such as shown in FIGS. 1 through 6. A humeral component 10 is shown engaging an ulnar component 50', which is identical to ulnar component 50 of FIGS. 4 through 6, except having a stem orientation for a left arm rather than right. As shown in FIG. 7, the spheroid end of humeral component 10 is received beneath the shoulders 57' of ulnar component 50' in a load bearing arrangement. Similarly, protuberant portion 53' of the head engaging portion of ulnar component 50' is received within slot 13 of humeral component 10.

In the exploded view of FIG. 7, part of the interior of bore 14 through humeral component 10 can be seen as well as the enlarged bore 16. A pivot pin 22 of stainless steel is received within a bearing pin 21 of high molecular weight polyethylene to form a bearing pin assembly. Pivot pin 22 is inserted into bearing pin 21 with groove 23 being engaged by annular shoulder 27 (FIG. 8). When the joint prosthesis is assembled and positioned within a patient, bearing pin 21 with pivot pin 22 mounted therein, is located by a snap fit through bores 14 and 54, which corresponds to bore 54' of FIGS. 5 and 6. As best shown in FIG. 8, with reference to the joint components shown in FIG. 7, the main body 28 of bearing pin 21 passes through bores 14 and 54' to maintain the prosthesis components in engagement. Head portion 24 of bearing pin 21 is received within wide bore portion 16 of the humeral component when the bearing pin assembly is fully inserted into the bores for the snap fit. A narrowed portion of pin 21, indicated at 26 in FIG. 8, is received within the portion of bore 14 of the humeral component between slot 13 and expanded bore 16. The portions of the pin assembly within bore 14 are sized to provide a tight fit between the humeral component and the pin assembly.

The snap-fit action of pin 21 occurs when annular shoulder 29 at the end of narrowed portion 26 is inserted into slot 13, expanding slightly larger than bore 14 after being slightly compressed while passing through bore 14. Bore 54' in the protuberant disc portion 53' is wider than bore 14 and also wider than the diameter of pin 21 along its portion 28 received within bore 54' permitting rocking, or wobble, of ulnar component 50' relative to humeral component 10. This motion is permitted because slot 13 is about 12% greater in width than the thickness of protuberant disc portion 53' of ulnar component 50'. When this "rocking" or wobble is permitted to occur, the load bearing between the joint components is, as described previously, between spheroid end 17 of the humeral component and receiving shoulders 57 of the ulnar component. The freedom of movement of the joint components relative to one another to a limited degree in axial rotation and translational motion provides a protective cushion against rotational stresses which would otherwise tend to loosen the joint stems as in rigidly hinged prosthetic joints.

This cushioning greatly reduces the stresses on the bone-cement interface along the cemented stems of the joint components after implantation. The metal on polyethylene bearing of the joint provides better wear than in an all-metal joint, and the size of the prosthesis is such that only a small portion of the olecranon process and the trochlea need be removed for implantation. Since most of the bone at the joint is retained, there is no direct contact between skin and the prosthesis, avoiding the problem of skin necrosis. Further, origins and insertions of muscles around the joint are not compromised due to the retention of most of the bone in the area of the joint. Since most of the natural elbow joint remains after implantation of the present prosthesis, later prosthesis revision remains possible if necessary.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention and the scope of the claims are desired to be protected.

What is claimed is:
1. An implantable prosthetic elbow joint comprising:
   a. a first component including,
      1. A first stem portion for affixing the first component to bone,
      2. a head portion on one end of the first stem portion having a continuous essentially spheroid surface interrupted by a slot, the head portion including a bore therethrough transverse to and intersecting said slot;
   b. a second component including
      1. a second stem portion for affixing the second component to bone.
      2. a head-engaging portion on one end of the second stem portion defining a cavity, a portion of which is essentially spheroid, receiving the essentially spheroid surface of the head portion, interrupted by a protuberant portion received in the slot of the head portion and having a bore therethrough aligned with the transverse bore of the head portion of the first component; and c. pin means extending through the bores of the protuberant portion and the head portion for attaching the first component to the second component, said protuberant portion having a thickness less than that of said slot and the pin means including a pin assembly sized to be loosely received in the bore through one of the joint components and tightly received in the bore through the other of the joint components.

2. The joint of claim 1 in which the bore in the second component has a greater diameter than the bore of the first component.

3. The joint of claim 1 in which the pin means comprises a flexible hollow bearing pin receiving a rigid pivot pin, said pin means extending through the first and second components, the pin means being received in a snap fit by the head portion of the first component on one side of the slot.

4. The joint of claim 3 in which the diameter of the bore through the second component is greater than the diameter of the pin assembly in the vicinity of the bore through the second component.

5. The joint of claim 1 in which the pin means comprises a flexible hollow bearing pin surrounding and retaining a rigid pivot pin, one end of the bore through the head portion of the first component being enlarged and defining a shoulder, the bearing pin having a first enlarged portion positioned within the bore of the second component and having a second enlarged portion bearing against said shoulder, the first enlarged portion of the bearing pin being slightly larger than the bore of the first component, whereby as the pin means is inserted the first enlarged portion of the bearing pin is forced past the bore of the first component and received in a snap fit within the bore of the second component.

6. The joint of claim 5 in which the first component is polyethylene and the second component is a surgically approved metal.

7. The joint of claim 1 in which the essentially spheriod surface of the head portion of the first component bears against the essentially spheriod surface of the second component in a load-bearing relationship, whereby load-bearing stresses on the pin means are reduced.

8. The joint of claim 7 in which the pin means comprises a flexible hollow bearing pin receiving a rigid pivot pin, said pin means extending through the first and second components, the pin means being received in a snap fit by the head portion of the first component on one side of the slot.

9. The joint of claim 8 in which the diameter of the bore through the second component is greater than the diameter of the pin assembly in the vicinity of the bore through the second component.

10. The joint of claim 9 in which the bore in the second component has a greater diameter than the bore of the first component.

* * * * *